United States Patent
Permeswaran et al.

(10) Patent No.: US 11,903,847 B2
(45) Date of Patent: Feb. 20, 2024

(54) PRESSURE SENSITIVE TRIAL INSTRUMENT AND METHOD

(71) Applicant: Zimmer Biomet Spine, Inc., Westminster, CO (US)

(72) Inventors: Vijay N Permeswaran, Le Mars, IA (US); Anup Gandhi, Superior, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 17/076,432

(22) Filed: Oct. 21, 2020

(65) Prior Publication Data

US 2021/0121304 A1 Apr. 29, 2021

Related U.S. Application Data

(60) Provisional application No. 62/925,897, filed on Oct. 25, 2019.

(51) Int. Cl.
*A61F 2/46* (2006.01)
*A61F 2/44* (2006.01)
*A61F 2/30* (2006.01)

(52) U.S. Cl.
CPC ........ *A61F 2/4611* (2013.01); *A61F 2/30734* (2013.01); *A61F 2/442* (2013.01); *A61F 2/4684* (2013.01); *A61F 2002/30448* (2013.01); *A61F 2002/30738* (2013.01)

(58) Field of Classification Search
CPC ............ A61F 2/4684; A61F 2002/4687; A61F 2002/4688; A61F 2/4611; A61F 2002/4615; A61F 2/4657; A61F 2002/4666
See application file for complete search history.

(56) References Cited

U.S. PATENT DOCUMENTS

| | | | | |
|---|---|---|---|---|
| 4,987,904 A | * | 1/1991 | Wilson | A61F 2/4684 73/104 |
| 2002/0156536 A1 | * | 10/2002 | Harris | A61F 2/32 623/22.17 |
| 2002/0165612 A1 | * | 11/2002 | Gerber | A61F 2/4684 623/17.11 |
| 2008/0065225 A1 | * | 3/2008 | Wasielewski | A61B 5/742 623/18.11 |
| 2010/0004657 A1 | * | 1/2010 | Dudasik | A61F 2/4611 606/86 A |
| 2013/0076157 A1 | * | 3/2013 | Stein | A61B 5/103 307/116 |

(Continued)

*Primary Examiner* — Matthew J Lawson
(74) *Attorney, Agent, or Firm* — Sheridan Ross P.C.

(57) ABSTRACT

An implant-trialing instrument for objectively determining a recommended implant size based at least in part on results of inserting a pressure sensitive trial implant into the intervertebral space. The trial implant instrument can include a handle coupled to a pressure sensitive trial. The handle can include an elongate shaft. The pressure sensitive trial implant can be disposed on a distal end of the elongate shaft and include a superior end plate surface configured to engage a first end plate of a first vertebral body and an inferior end plate configured to engage a second end plate of a second vertebral body. The pressure sensitive trial implant also includes a pressure sensitive film disposed on at least one of the superior end plate and the inferior end plate.

24 Claims, 5 Drawing Sheets

(56) References Cited

U.S. PATENT DOCUMENTS

| | | | |
|---|---|---|---|
| 2013/0204157 A1* | 8/2013 | Clark | A61B 5/4585 |
| | | | 73/862.68 |
| 2014/0296860 A1* | 10/2014 | Stein | A61B 34/20 |
| | | | 606/90 |
| 2015/0282797 A1* | 10/2015 | O'Neil | A61B 1/3135 |
| | | | 606/279 |
| 2019/0125293 A1* | 5/2019 | Behzadi | A61F 2/468 |
| 2019/0133547 A1* | 5/2019 | Behzadi | A61B 7/023 |
| 2020/0093613 A1* | 3/2020 | Arramon | A61F 2/30771 |
| 2020/0214855 A1* | 7/2020 | McAuliffe | A61F 2/4657 |
| 2020/0297513 A1* | 9/2020 | Zellmer | A61B 34/25 |

* cited by examiner

PRESSURE SENSITIVE TRIAL INSTRUMENT AND METHOD

CLAIM OF PRIORITY

This application claims the benefit of U.S. Provisional Patent Application Ser. No. 62/925,897, filed on Oct. 25, 2019, the benefit of priority of which is claimed hereby, and which is incorporated by reference herein in its entirety.

TECHNICAL FIELD

This document pertains generally, but not by way of limitation, to devices, instruments, and methods used during spinal surgical procedures, such those involving implantation of cervical prosthetic replacement discs. More specifically, but not by way of limitation, the present application relates to instruments for measuring the intervertebral disc space and selecting a properly sized prosthesis for implantation.

BACKGROUND

Spinal deformity correction often involves implantation of a prosthetic device to replace damaged or missing vertebral disc material. For example, in the cervical spine Zimmer Biomet provide a device marketed under the Mobi-C® name that enables disc replacement while maintaining native range of motion. The Mobi-C® device is designed to replicate the natural mobility provided by a patient's vertebral disc material. One important step in the disc replacement procedure is sizing the intervertebral disc space to select the proper size of prosthetic disc. Prosthetic systems, such as Mobi-C® from Zimmer Biomet, often include a set of trialing instruments that replicate the prosthesis sizes for use in the procedure. Trialing instruments, typically, mimic the overall dimensions of each prosthesis size with an attached handle for insertion and removal. The trialing process often involves multiple additional x-ray exposures for the patient to allow a surgeon to ensure proper vertebral endplate coverage as well as height. Typically, available trialing instruments are tools for use by a surgeon, but still require judgment and experience from the surgeon to obtain a proper fit.

Overview

The present inventors have recognized, among other things, that a problem to be solved can include the prevention of the use of over-sized intervertebral implants. Research conducted by the present inventors indicates that a properly sized Mobi-C® implant maintains range of motion in 1 and 2 level procedures that is nearly identical to native intact spinal levels. However, selecting too tall of an implant by as little as 1 mm can produce a 15% drop in range of motion across the cervical spine (C2 to T1) and over a 50% drop in range of motion at the corrected level. The research shows that overstuffing effectively creates a quasi-fusion at the replacement level. Currently available trialing instruments fail to provide any objective measures or output to assist in guiding a surgeon in selecting a properly sized implant (prosthesis). The present inventors have developed a trialing instrument that can provide objective feedback to assist a surgeon in selecting the proper implant size. In an example, a set of trailing instruments spanning corresponding to the available implant sizes are provided with pressure sensitive material adhered to the end plates of the trial implant. In this example, the pressure sensitive material provides an objective visual feedback to the surgeon regarding the fit of the trial within the vertebral disc space. In an example, the end plate surfaces of the trialing instruments can be covered in a single use pressure sensitive film that creates a pressure map through a color density created when the applied pressure bursts microbubbles of ink within the film. The following specification further details instruments and methods for minimizing the loss of range of motion through proper implant size selection by providing objective measurements of the disc space.

This overview is intended to provide an overview of subject matter of the present patent application. It is not intended to provide an exclusive or exhaustive explanation of the invention. The detailed description is included to provide further information about the present patent application.

Figure 1A:
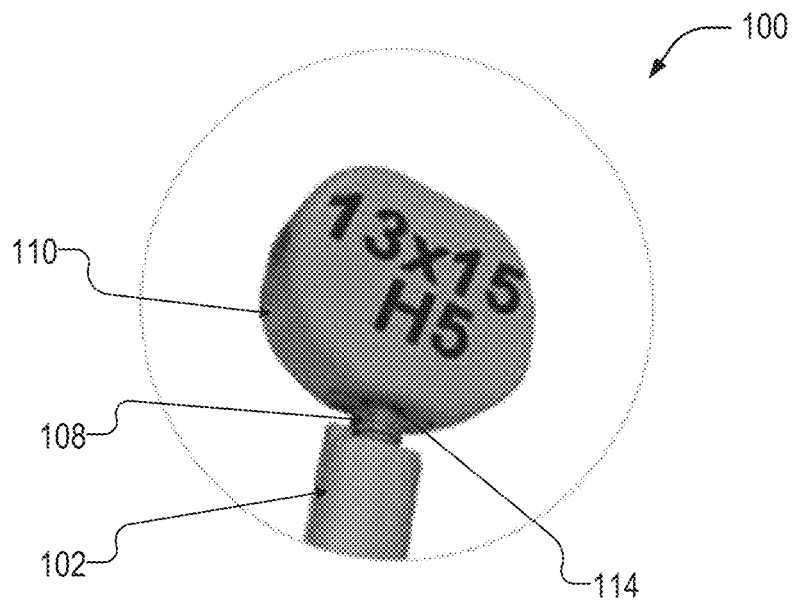
FIG. 1A is a perspective view of an implant sizing instrument, in accordance with at least one example of the disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It should be understood that the following detailed description of embodiments of the present invention are exemplary in nature and are not intended to constitute limitations upon the present invention. It is also to be understood that variations of the exemplary embodiments contemplated by one of ordinary skill in the art shall concurrently fall within the scope and spirit of the invention.

Figure 1B:
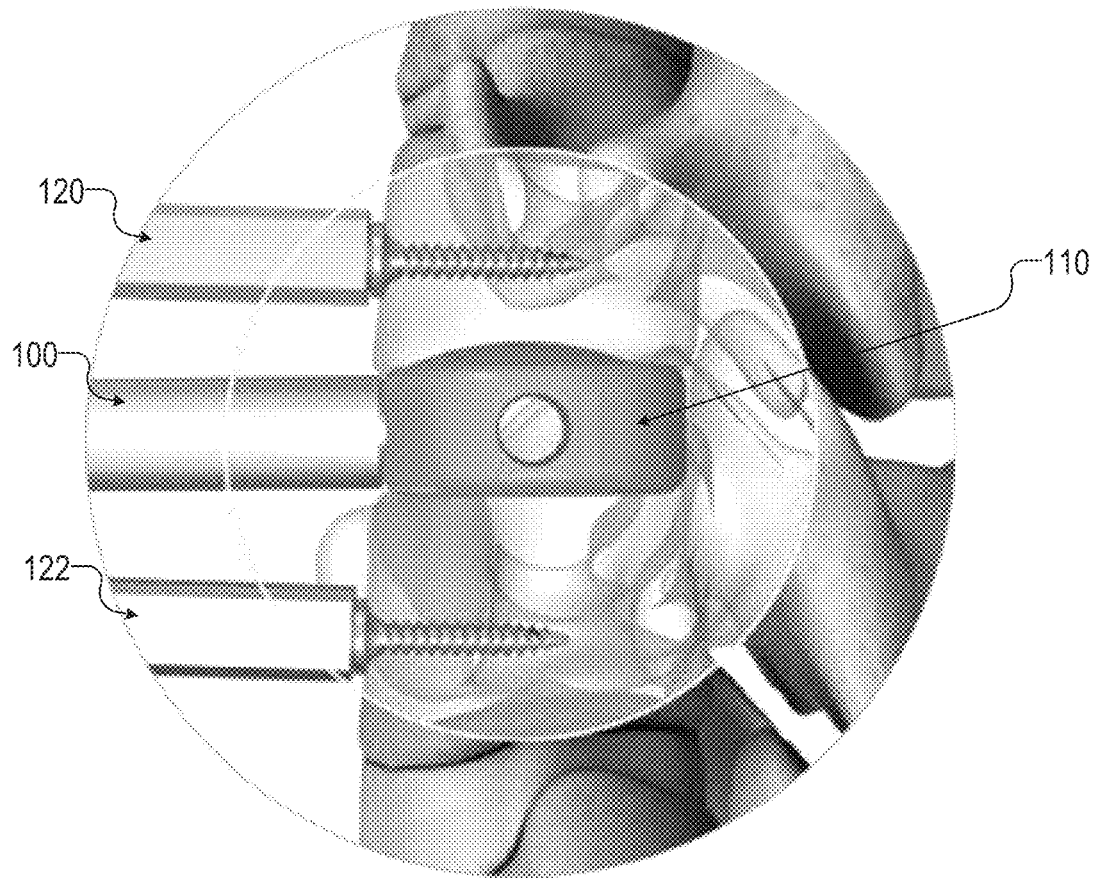
FIG. 1B is a perspective view illustrating an implant sizing instrument in use within a patient, in accordance with at least one example of the disclosure.

FIGS. 1A-1D illustrate an implant sizing instrument in accordance with various examples of the present disclosure. FIG. 1A is a perspective view of an implant sizing instrument, in accordance with at least one example of the disclosure. In this example, the implant sizing instrument 100 can include an elongate extension 102 coupled to a pressure sensitive trial 110 via a coupling shaft 108. The coupling shaft 108 can thread into a threaded coupling bore 114 on the pressure sensitive trial 110. FIG. 1B provides an illustration of the implant sizing instrument 100 in use placing the pressure sensitive trial 110 between two vertebral bodies. In this example, the vertebral bodies can be distracted during insertion through use of a superior distractor 120 and an inferior distractor 122 (collectively referred to in some examples as a caspar distractor or simply a distractor). In general, the pressure sensitive trial 110 can include end plate surfaces (e.g., superior and inferior surfaces designed to engage end plates of opposing vertebral bodies) that are covered in a pressure sensitive film. In an example, the pressure sensitive film can be a product such as Fujifilm Prescale, which includes a layer of micro-encapsulated color forming material and a layer of color-developing material. Prescale comes in two types a mono-sheet where the color forming material and color-developing material are within the same sheet, and a two-sheet type where one sheet contains the micro-encapsulated color-forming material and the other sheet contains the color-developing material. In either type, the film turns various degrees of red when exposed to surface pressure. The darker and/or denser the color the higher the amount of surface pressure. The film is designed to capture peak pressure readings. The film functions by the microcapsules of color-forming material being broken and reacting with the color-developing agent when pressure is applied. The film is available to measure pressures in a wide range (e.g., 0.05-300 MPa (7.25 psi-43,500 psi). The film can be a thin as 200 μm.

Figure 1C:
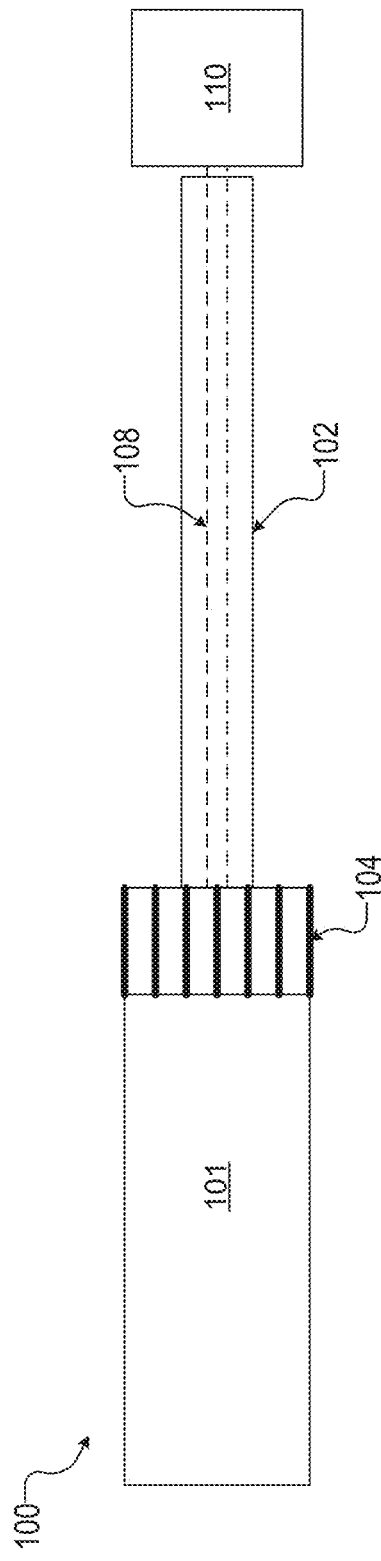
FIG. 1C is a top view line drawing of an implant sizing instrument, in accordance with at least one example of the disclosure.
Figure 1D:
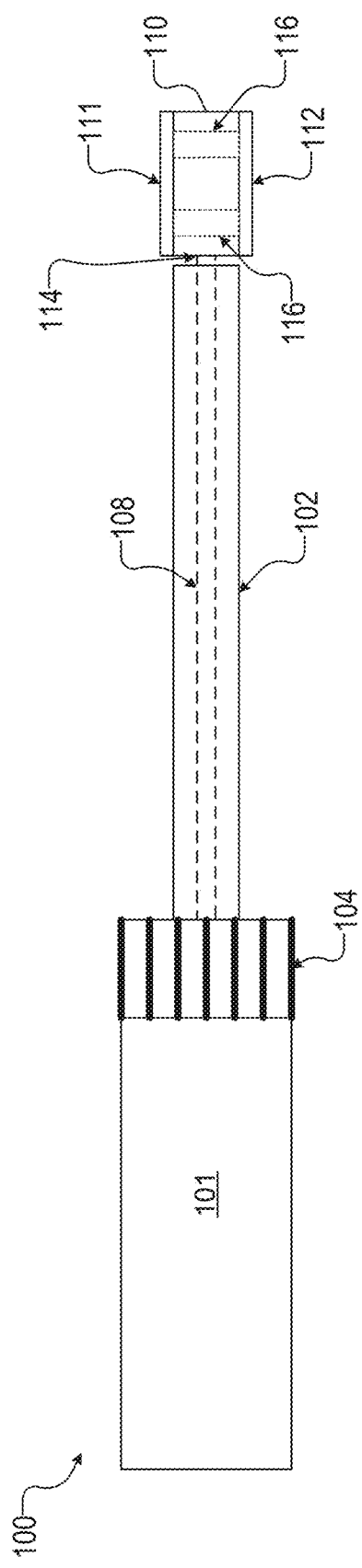
FIG. 1D is a side view line drawing of an implant sizing instrument, in accordance with at least one example of the disclosure.

FIG. 1C is a top view line drawing of the implant sizing instrument 100, in accordance with at least one example of the disclosure. In this example, the implant sizing instrument 100 is illustrated as including a handle assembly 101, an elongate extension 102, a coupling knob 104, a coupling shaft 108, and a pressure sensitive trial 110. The coupling shaft 108 can include a threaded distal end that couples to a threaded bore 114 (see FIG. 1D) on the pressure sensitive trial 110. FIG. 1D is a side view line drawing of the implant sizing instrument 100. In the side view of the pressure sensitive trial 110 the superior and inferior layers of pressure sensitive film are shown (e.g., superior film 111 and inferior film 112). In certain examples, the pressure sensitive film is adhered to the pressure sensitive trial 110 via a permanent or moveable adhesive. In other examples, the pressure sensitive film can be held in place by a film sleeve, illustrated in FIG. 1D as film sleeve 116 (two strips of material along lateral sides of the pressure sensitive trial 110). In another example, the film sleeve can be in the form a continuous cylindrical film the fits tightly around the pressure sensitive trial 110. Different approaches to retaining the pressure sensitive film are provided to allow for fully disposable (single use) trials, such as with permanently adhered film as well as reusable trials, such as with removal adhesive or use of a film sleeve.

Figure 2:
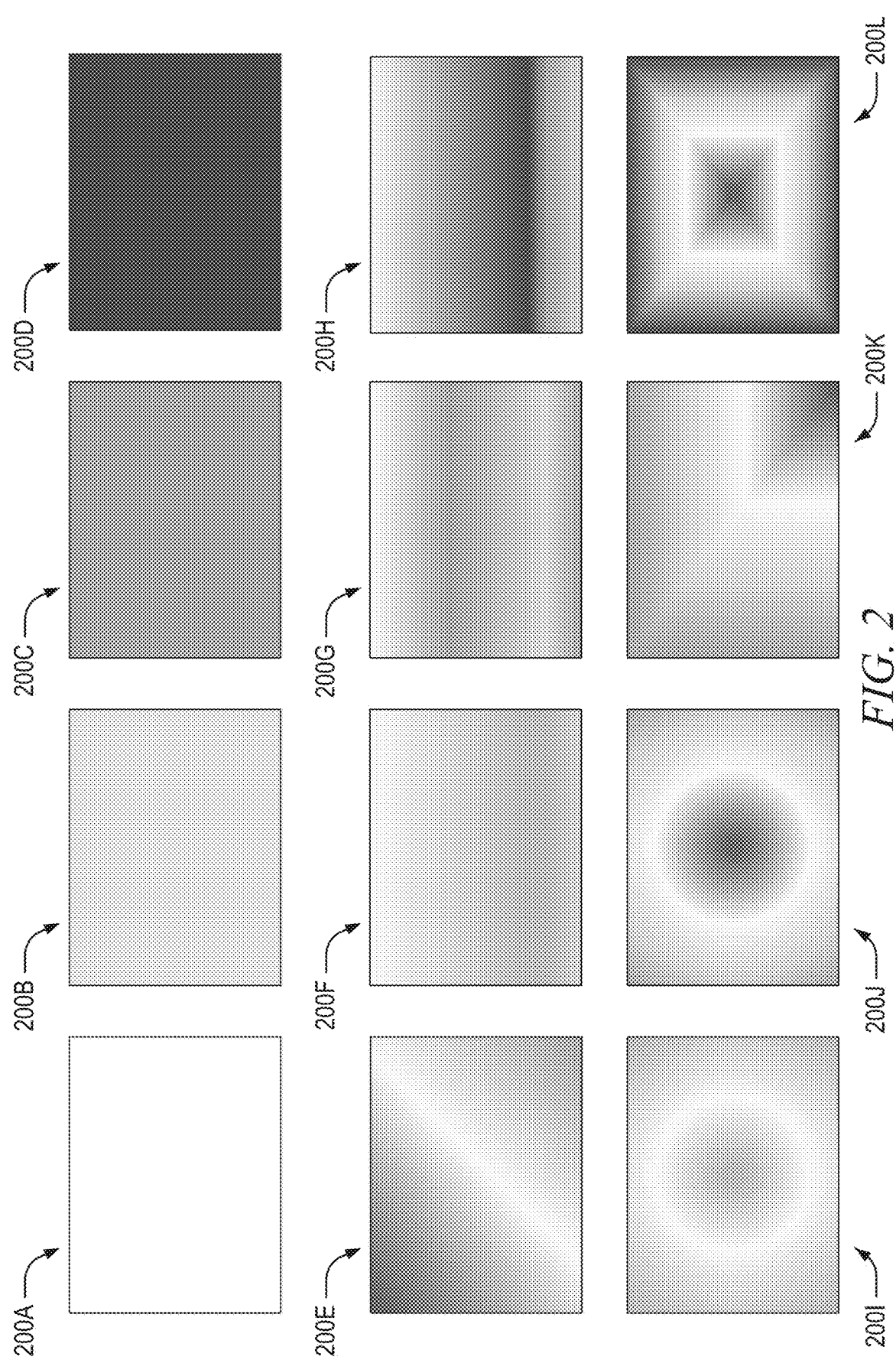
FIG. 2 is a series of illustrations depicting pressure sensitive film after use on an implant sizing instrument, in accordance with at least one example of the disclosure.

FIG. 2 is a series of illustrations depicting a surface covered in pressure sensitive film (200A-200L) after use on an implant sizing instrument, in accordance with at least one example of the disclosure. Surface pressure applied to the pressure sensitive film used on the pressure sensitive trial 110 leaves a permanent impression through color changing chemical reaction within the film (as described above). The pressure sensitive film surface examples (200A-200L) illustrate different potential results of utilizing a pressure sensitive film on the surface of a trial instrument. The examples shown are strictly illustrations and may not reflect the exact results of real-world use of the pressure sensitive film. However, the example do accurately represent how the pressure sensitive film captures pressure measurements across a surface. Examples 200A-200D, illustrate different (increasing) amounts of uniform pressure received by a surface with pressure sensitive film applied. Example 200A illustrates a surface that did not receive pressure above a threshold pressure for the particular version of the pressure sensitive film (e.g., did not break any micro-encapsulated color-forming material). Examples, 200B through 200D illustrate a surface that received increasing amounts of pressure above a lower threshold pressure, with example 200D illustrating a surface that received at least an upper threshold pressure (e.g., a situation where all of the micro-encapsulated color-forming material in the film was broken by the applied pressure). The film used for a pressure sensitive trial 110 is selected to have the desired intervertebral pressure fall between a film's upper and lower threshold pressures, which will allow the surgeon to compare the color and/or density of color change to a known standard. The remaining examples 200E-200L illustrate different gradient or point loading that may be exhibited with use of the pressure sensitive trial 110. The known standard will provide guidance on an allowable level of gradient or point loading before a different size trial is recommended.

In an example, analysis of the pressure sensitive trial 110 after trialing in an intervertebral space can be conducted via a computerized system. Fujifilm produces a pressure distribution mapping application for the Prescale product. The pressure distribution mapping application can be utilized to produce multi-faceted measurement data from pressure sensitive film. The measurement data can then be compared to known acceptable ranges of comparable measurement data to determine whether the selected size of the pressure sensitive trial should be used in selection of the final implant. Utilizing the Fujifilm software involves a computer system with a scanner or camera to digitize the exposed pressure sensitive film. The analysis software can also provide a three-dimensional (3D) visualization of the pressure distribution across the surface of the pressure sensitive trial 110, which can also be utilized in determining proper implant size. Accordingly, the Fujifilm software in combination with a properly equipped and programmed computer-system can automate implant size selection using pressure sensitive trials as discussed herein.

Figure 3:
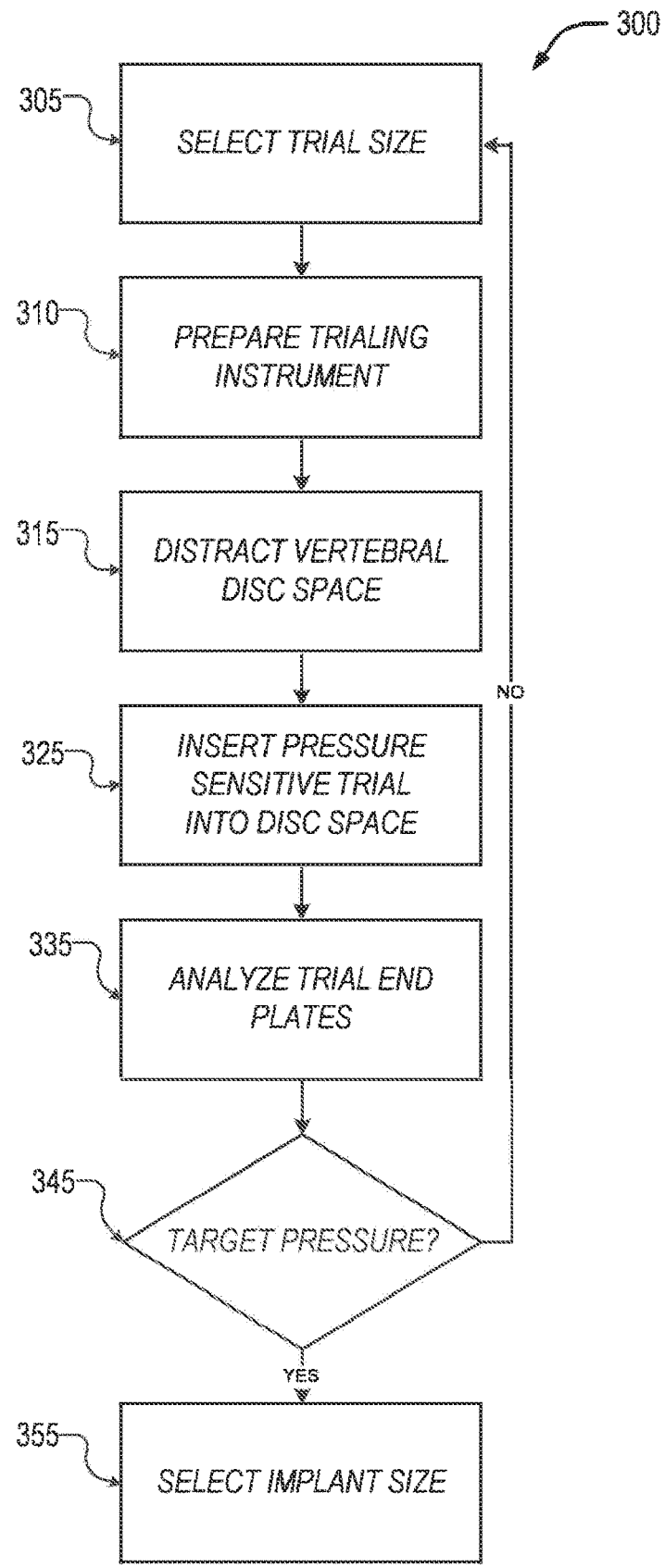
FIG. 3 is a flow chart illustrating a technique for operating an implant sizing instrument, in accordance with at least one example of the disclosure.

FIG. 3 is a flow chart illustrating a technique 300 for sizing an implant using an implant sizing instrument, in accordance with at least one example of the disclosure. In this example, the technique 300 can include operations such as: selecting a trial size at 305, preparing an instrument at 310, distracting the disc space at 315, inserting the trial at 325, analyzing the trial at 335, determining whether target pressure was measured at 345, and selecting an implant size at 355.

In an example, the technique 300 can begin at 305 with selection of a trial size. The trial size can be selected based on initial surgeon judgement regarding the size of the disc space prepared prior to starting technique 300. The implant kit will include trials for each different size in the range of implant sizes available. The trial selected will include or have added to it the pressure sensitive film. At 310, the technique 300 can continue with the surgeon or assistant preparing the implant sizing instrument, such as implant sizing instrument 100. Preparing the implant sizing instrument can include coupling the selected trial to the distal end of the instrument as well as applying the pressure sensitive film to at least one end plate surface of the trial (in cases where the pressure sensitive film isn't already adhered to the trial).

At 315, the technique 300 can optionally continue with distracting the vertebral disc space prepared for an implant. Distraction with a distraction instrument, such as with superior distractor 120 and inferior distractor 122, is optional as the trials are typically shaped to allow for insertion without distraction. However, distraction is useful to avoid applying pressure to the pressure sensitive film prior to the trial being in the desired implant location. At 325, the technique 300 can continue with the trial being inserted into the disc space using the implant sizing instrument. Once the trial is inserted into the desired location the distraction (if any) can be removed to allow the vertebral bodies to apply pressure to the pressure sensitive trial. After the vertebral bodies are allowed to contact the pressure sensitive trial, the pressure sensitive trial can be removed (with or without distraction). At 335, the technique 300 can continue with analysis of the pressure sensitive film on the trial end plates being conducted. As discussed above, the analysis can be via human comparison to known standards or computerized analysis. The analysis can include comparing color and/or color density against known or targeted standards, such as a particular shade of red and a particular uniformity of color across the surface.

At 345, the technique 300 continues with determining whether the pressure sensitive surfaces sufficiently match the known standard. Sufficiency of match can be subjective, but the surgical technique will include guidelines to assist in making the judgement. The surgical technique may include a range of color swatches considered acceptable, as well as color swatches considered above or below certain thresholds. In an example, the surgical guide can include a upper acceptable color swatch and a lower acceptable color swatch. Additionally, the surgical technique can include guidelines on uniformity, which may be combined with color swatches to assist in comparison. For example, the surgical guide may indicate that no hot-spot bigger than % inch may be darker than a certain color swatch. If it is determined at 345 that the target or desired pressure was observed, then the technique 300 can conclude at 355, otherwise the technique 300 reverts back to 305 to select a different trial size and proceed through the technique again. At 355, the technique concludes with selection of the implant size corresponding to the trial size that resulted in achieving the desired intervertebral disc space pressure.

Figure 4:
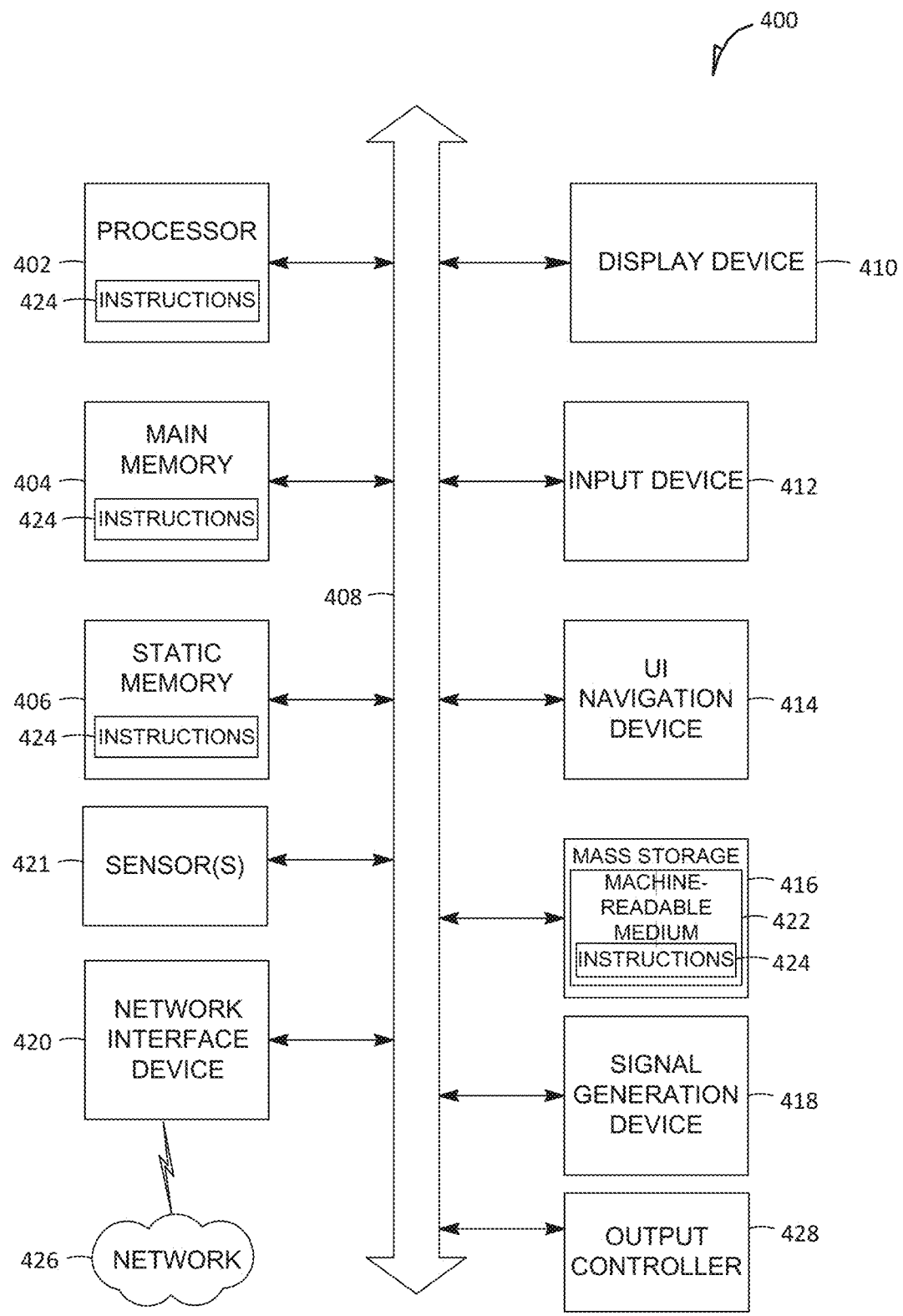
FIG. 4 is a block diagram of an example machine upon which any one or more of the techniques discussed herein may perform in accordance with some embodiments.

FIG. 4 illustrates a block diagram of an example machine 400 upon which any one or more of the techniques discussed herein may perform in accordance with some embodiments. The machine 400 can also host any of the user interfaces discussed herein. In alternative embodiments, machine 400 may operate as a standalone device or may be connected (e.g., networked) to other machines. In a networked deployment, machine 400 may operate in the capacity of a server machine, a client machine, or both in server-client network environments. In an example, machine 400 may act as a peer machine in peer-to-peer (P2P) (or other distributed) network environment. Machine 400 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 400 may include hardware processor 402 (e.g., a central processing unit (CPU), a graphics processing unit (GPU), a hardware processor core, or any combination thereof), main memory 404 and static memory 406, some or all of which may communicate with each other via interlink (e.g., bus) 408. Machine 400 may further include display unit 410, alphanumeric input device 412 (e.g., a keyboard), and user interface (UI) navigation device 414 (e.g., a mouse). In an example, display unit 410, input device 412 and UI navigation device 414 may be a touch screen display. In another example, input device 412 can include a scanner or camera device. Machine 400 may additionally include storage device (e.g., drive unit) 416, signal generation device 418 (e.g., a speaker), network interface device 420, and one or more sensors 421, such as a global positioning system (GPS) sensor, compass, accelerometer, or other sensor. Machine 400 may include output controller 428, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 416 may include machine readable medium 422 on which is stored one or more sets of data structures or instructions 424 (e.g., software) embodying or utilized by any one or more of the techniques or functions described herein. Instructions 424 may also reside, completely or at least partially, within main memory 404, within static memory 406, or within hardware processor 402 during execution thereof by machine 400. In an example, one or any combination of hardware processor 402, main memory 404, static memory 406, or storage device 416 may constitute machine readable media.

While machine readable medium 422 is illustrated as a single medium, the term "machine readable medium" may include a single medium or multiple media (e.g., a centralized or distributed database, and/or associated caches and servers) configured to store the one or more instructions 424. The term "machine readable medium" may include any medium that is capable of storing, encoding, or carrying instructions for execution by machine 400 and that cause machine 400 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 424 may further be transmitted or received over communications network 426 using a transmission medium via network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 420 may include one or more physical jacks (e.g., Ethernet, coaxial, or phone jacks) or one or more antennas to connect to communications network 426. In an example, network interface device 420 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 400, and includes digital or analog communications signals or other intangible medium to facilitate communication of such software.

The systems, devices and methods discussed in the present application can be useful in performing registration processes of fiducial markers with robotic surgical systems, such as by improving the accuracy of the registration process. In particular, the systems, devices and methods described herein facilitate more precise engagement between a pointer probe tip and a fiducial marker and better recognition of proper engagement between a pointer probe tip and the fiducial marker by an operator or surgeon. Such benefits can reduce error in the registration process, which can correlate to reduced error in performing a medical procedure on a patient.

VARIOUS NOTES & EXAMPLES

See example claims included below.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A trial implant instrument comprising:
   a handle including an elongate shaft;
   a pressure sensitive trial coupled to the elongate shaft, the pressure sensitive trial including a superior end plate exterior surface configured to engage a first end plate of a first vertebral body, a separate inferior end plate exterior surface configured to engage a second end plate of a second vertebral body, and one or more lateral side surfaces between the superior end plate exterior surface and the inferior end plate exterior surface, the pressure sensitive trial having a non-adjustable thickness between the superior end plate exterior surface and the inferior end plate exterior surface; and
   a pressure sensitive film disposed on at least one of the superior end plate exterior surface and the inferior end plate exterior surface, and further disposed on at least a portion of the one or more lateral side surfaces,
   wherein the pressure sensitive film is operable to indicate whether a predetermined target pressure is achieved following contact of the first end plate of the first vertebral body to the superior end plate exterior surface, and further following contact of the second end plate of the second vertebral body to the inferior end plate exterior surface.

2. The trial implant instrument of claim 1, wherein the pressure sensitive film is disposed on both the superior end plate exterior surface and the inferior end plate exterior surface.

3. The trial implant instrument of claim 1, wherein the pressure sensitive film is adhered to at least one of the superior end plate exterior surface and the inferior end plate exterior surface with an adhesive material.

4. The trial implant instrument of claim 1, wherein the one or more lateral side surfaces includes at least two lateral side surfaces, and wherein the pressure sensitive film is held in position on at least one of the superior end plate exterior surface and the inferior end plate exterior surface with an exterior film sleeve wrapping around the at least two lateral side surfaces of the pressure sensitive trial.

5. The trial implant instrument of claim 4, wherein the pressure sensitive trial is reusable and the pressure sensitive film is disposable.

6. The trial implant instrument of claim 1, wherein the pressure sensitive trial with the pressure sensitive film disposed on at least one of the superior end plate exterior surface and the inferior end plate exterior surface is single use.

7. The trial implant instrument of claim 1, wherein the pressure sensitive trial includes a threaded bore, and the elongate shaft includes a threaded distal end configured to removably couple to the threaded bore.

8. The trial implant instrument of claim 7, wherein the handle further includes a coupling knob connected to the elongate shaft and configured to receive rotational input and transmit the rotational input to rotate the elongate shaft.

9. A implant sizing system comprising:
 an instrument handle including an elongate shaft extending from a distal end; and
 a plurality of pressure sensitive trial implants couplable to a distal end of the elongate shaft, each pressure sensitive trial implant of the plurality of pressure sensitive trial implants corresponding to a predetermined size for an implant, each pressure sensitive trial implant of the plurality of pressure sensitive trial implants having a non-adjustable thickness between a superior end plate exterior surface and a separate inferior end plate exterior surface, each pressure sensitive trial implant of the plurality of pressure sensitive trial implants including one or more lateral side surfaces between the superior end plate exterior surface and the inferior end plate exterior surface,
 wherein at least one of the superior end plate exterior surface and the inferior end plate exterior surface of each pressure sensitive trial implant is covered in a pressure sensitive film, wherein the pressure sensitive film is further disposed on at least a portion of the one or more lateral side surfaces,
 wherein the pressure sensitive film is configured to change color in localized areas in response to a pressure or force applied to the pressure sensitive trial implant, wherein the pressure sensitive film is operable to indicate whether a predetermined target pressure is achieved following contact of a first end plate of a first vertebral body to the superior end plate exterior surface, and
 further following contact of a second end plate of a second vertebral body to the inferior end plate exterior surface, wherein the predetermined target pressure corresponds to the predetermined size for the implant.

10. The implant sizing system of claim 9, further comprising a vertebral body distraction instrument configured to engage a superior vertebral body and an inferior vertebral body to enable distraction of a disc space between the superior vertebral body and the inferior vertebral body to allow insertion of a pressure sensitive trial implant of the plurality of pressure sensitive trial implants.

11. The implant sizing system of claim 9, wherein the pressure sensitive film is disposed on both the superior end plate exterior surface and the inferior end plate exterior surface of each pressure sensitive trial implant of the plurality of pressure sensitive trial implants.

12. The implant sizing system of claim 9, wherein the pressure sensitive film is adhered to the at least one superior end plate exterior surface and inferior end plate exterior surface of each pressure sensitive trial implant with an adhesive material.

13. The implant sizing system of claim 9, wherein the one or more lateral side surfaces includes at least two lateral side surfaces, and wherein the pressure sensitive film is held in position on the at least one superior end plate exterior surface and inferior end plate exterior surface with an exterior film sleeve wrapping around the at least two lateral side surfaces of each pressure sensitive trial implant.

14. The implant sizing system of claim 13, wherein each pressure sensitive trial implant is reusable and the pressure sensitive film is disposable.

15. The implant sizing system of claim 9, wherein each pressure sensitive trial implant with the pressure sensitive film disposed on the at least one superior end plate exterior surface and inferior end plate exterior surface is single use.

16. The implant sizing system of claim 9, wherein each pressure sensitive trial implant includes a threaded bore, and the distal end of the elongate shaft is threaded to removably couple to the threaded bore.

17. The implant sizing system of claim 16, wherein the handle further includes a coupling knob connected to the elongate shaft and configured to receive rotational input and transmit the rotational input to rotate the elongate shaft.

18. A method for implant sizing, the method comprising:
 selecting an implant size including obtaining a pressure sensitive trial implant corresponding to the selected implant size;
 preparing a trialing instrument including coupling the pressure sensitive trial implant to a distal end of an elongate shaft portion of the trialing instrument, the pressure sensitive trial implant having a non-adjustable thickness between a superior end plate exterior surface and a separate inferior end plate exterior surface, the pressure sensitive trial implant including one or more lateral side surfaces between the superior end plate exterior surface and the inferior end plate exterior surface, wherein at least one of the superior end plate exterior surface and the inferior end plate exterior surface of the pressure sensitive trial implant is covered in a pressure sensitive film, and wherein the pressure sensitive film is further disposed on at least a portion of the one or more lateral side surfaces;
 trialing the pressure sensitive trial implant in an intervertebral disc space between a first vertebral body and a second vertebral body, the intervertebral disc space prepared to receive an intervertebral implant; and
 determining whether the selected implant size is correct based at least in part on comparing a state of the pressure sensitive film disposed on at least one of the superior end plate exterior surface and the inferior end plate exterior surface of the pressure sensitive trial implant to a known standard, wherein the pressure sensitive film is operable to indicate whether a predetermined target pressure is achieved following contact of a first end plate of the first vertebral body to the superior end plate exterior surface, and further following contact of a second end plate of the second vertebral body to the inferior end plate exterior surface, wherein the predetermined target pressure corresponds to the selected implant size.

19. The method for implant sizing of claim 18, further comprising distracting the intervertebral disc space prior to trialing the pressure sensitive trial implant.

20. The method for implant sizing of claim 18, further comprising disposing of the pressure sensitive trial implant after use.

21. The method for implant sizing of claim 18, wherein comparing the state of the pressure sensitive film to the known standard indicates that the selected implant size is incorrect.

22. The method for implant sizing of claim 21, further comprising:
    selecting a second implant size based on the indication that the selected implant size is incorrect;
    preparing the trialing instrument including coupling a second pressure sensitive trial implant to the distal end of the elongate shaft portion, wherein the second pressure sensitive trial implant corresponds to the second implant size, the second pressure sensitive trial implant having a second, different non-adjustable thickness between a second superior end plate exterior surface and a second separate inferior end plate exterior surface, the second pressure sensitive trial implant including one or more second lateral side surfaces between the second superior end plate exterior surface and the second inferior end plate exterior surface, wherein at least one of the second superior end plate exterior surface and the second inferior end plate exterior surface of the second pressure sensitive trial implant is covered in a second pressure sensitive film, and wherein the second pressure sensitive film is further disposed on at least a portion of the one or more second lateral side surfaces;
    trialing the second pressure sensitive trial implant; and
    determining whether the second implant size is correct based at least in part on comparing a state of the second pressure sensitive film disposed on at least one of the second superior end plate exterior surface and the second inferior end plate exterior surface of the second pressure sensitive trial implant to the known standard.

23. The method for implant sizing of claim 18, wherein comparing the state of the second pressure sensitive film includes examining color changes across a surface of the at least one of the second superior end plate exterior surface and the second inferior end plate exterior surface with the second pressure sensitive film.

24. The method for implant sizing of claim 18, wherein comparing the state of the pressure sensitive film includes comparing color, color density, or color intensity to the known standard.

* * * * *